(12) United States Patent
Hahn

(10) Patent No.: US 6,700,031 B1
(45) Date of Patent: Mar. 2, 2004

(54) THERAPEUTIC BANDAGE WITH MASSAGING PROJECTORS

(76) Inventor: Matthias Hahn, Konrad-Adenauer-Strasse 84, D-67731 Ottersbach (DE)

(*) Notice: Subject to any disclaimer, the term of this patent is extended or adjusted under 35 U.S.C. 154(b) by 0 days.

(21) Appl. No.: 10/049,206

(22) PCT Filed: Jul. 28, 2000

(86) PCT No.: PCT/DE00/02494
§ 371 (c)(1),
(2), (4) Date: May 3, 2002

(87) PCT Pub. No.: WO01/10370
PCT Pub. Date: Feb. 15, 2001

(30) Foreign Application Priority Data

Aug. 9, 1999 (DE) .......................... 199 37 535

(51) Int. Cl.[7] .................. A61F 13/40; A61H 23/00; A61H 7/00; A61B 17/03
(52) U.S. Cl. ................ 602/41; 606/204; 606/201; 602/60; 602/53; 602/48; 607/3; 601/15; 601/151; 601/134
(58) Field of Search .............. 601/15, 21, 148–152, 601/143, 134; 2/115, 69; 607/3, 44; 602/43, 53, 58, 41, 62, 67, 60; 606/204, 201

(56) References Cited

U.S. PATENT DOCUMENTS

| | | | |
|---|---|---|---|
| 3,888,242 A | 6/1975 | Harris et al. | 601/152 |
| 5,381,558 A | 1/1995 | Lo | 601/134 |
| 5,607,749 A | 3/1997 | Strumor | |
| 5,769,803 A | 6/1998 | Brossard | |
| 6,273,866 B2 | 8/2001 | Thomas et al. | 601/151 |
| 6,361,512 B1 | 3/2002 | Mackay et al. | 601/150 |
| 6,485,444 B1 | 11/2002 | Gershov | 601/138 |

FOREIGN PATENT DOCUMENTS

| | | |
|---|---|---|
| DE | 82289 | 3/1894 |
| DE | 4219698 | 12/1993 |
| DE | 19611888 | 10/1997 |
| DE | 19725648 | 8/1998 |
| FR | 1367724 | 6/1964 |
| JP | 11235372 | 8/1999 |
| WO | 97/49306 | 12/1997 |

*Primary Examiner*—Danton D. DeMille
(74) *Attorney, Agent, or Firm*—Rader, Fishman & Grauer PLLC

(57) ABSTRACT

A therapeutic bandage including a therapeutic surface having massage projections for contacting and massaging the body part to be treated. The therapeutic bandage is removably secured to the wearer by way of a closure element.

15 Claims, 6 Drawing Sheets

Fig. 6
Fig. 7
Fig. 8
Fig. 9
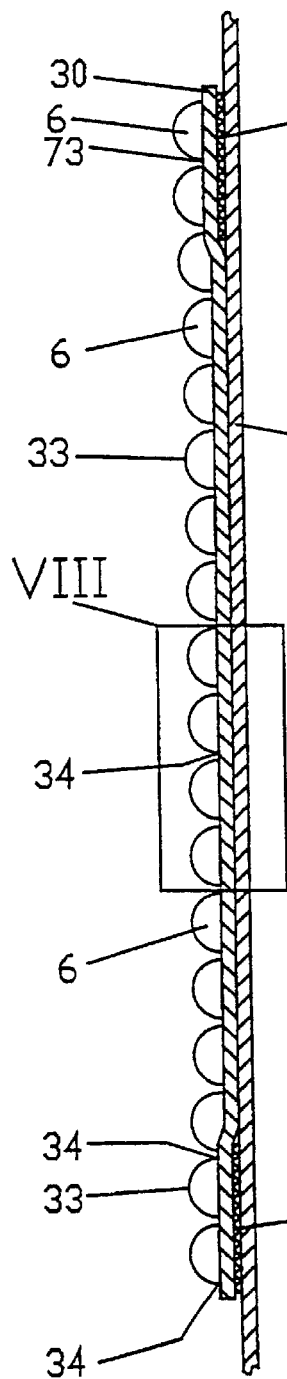
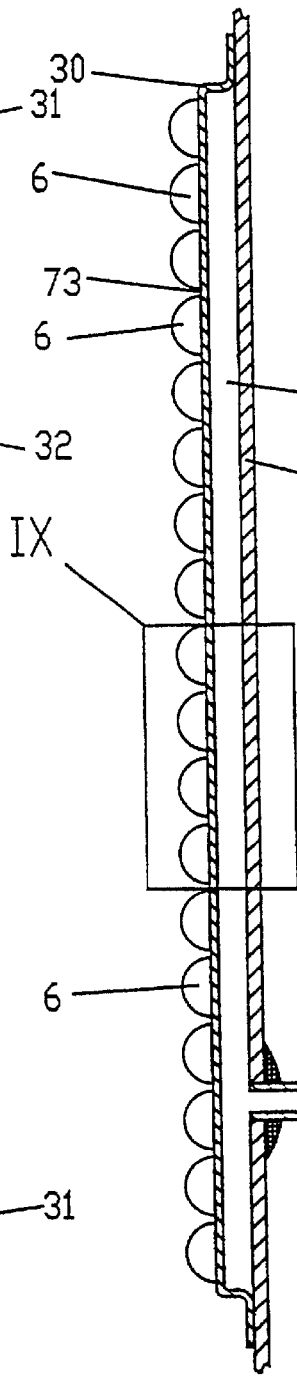
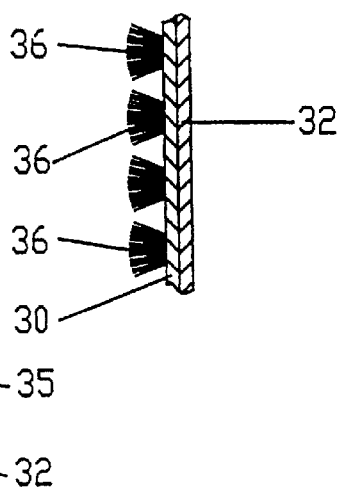
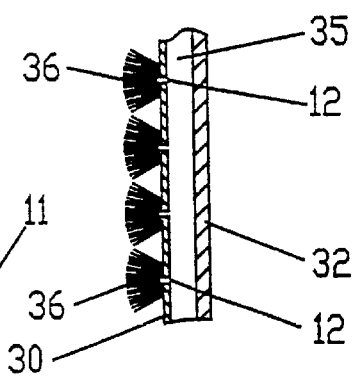

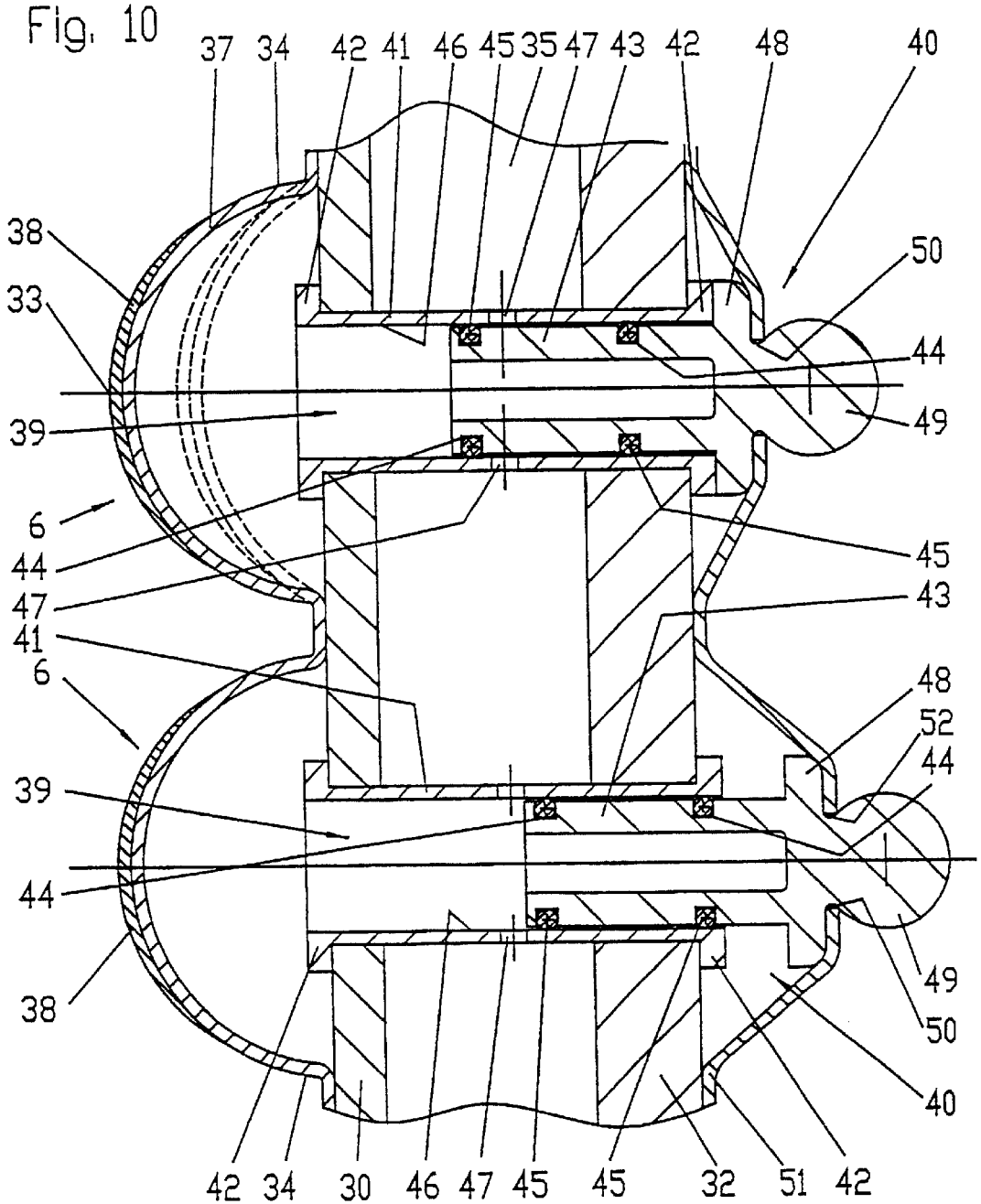
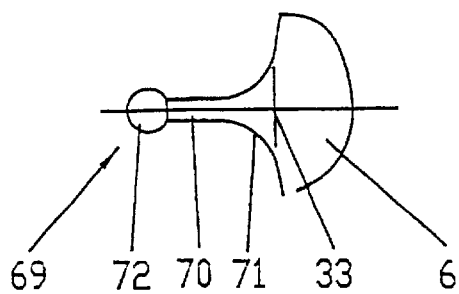

THERAPEUTIC BANDAGE WITH MASSAGING PROJECTORS

TECHNICAL FIELD

The invention relates to a therapeutic bandage having at least one therapeutic surface for a body part to be treated with massaging projections arranged on said therapeutic surface and pointing in the direction of the body part to be treated, said therapeutic bandage being removably secured to said body part by means of a closure element.

BACKGROUND OF THE INVENTION

DE-A-196 11 888 discloses a support bandage which has a double wall and which, in the use state, fits tightly around the body to be supported, said bandage being able to be prestressed by means of tightening straps which are connected to a fairly large section of bandage, which lies opposite the wearer's back in the wearing position, and which tightening straps prestress the support part and are made of a material which generates prestressing, for example rubber, plastic or the like.

In addition, DE-C-197 25 648 discloses a flexible orthopedic bandage which, in the open state, can be placed around a body part and can then be closed by means of a quick-closure element. In the area of the quick-closure element, the bandage has a means for temporarily stiffening this area during opening and/or closing of the bandage.

The aforementioned bandages are used only to support a weakened body part. Additional treatment of this body part is not possible. For the latter purpose, massage articles are normally used, for example brushes, balls, gloves and the like, with which the body part to be treated is massaged if necessary. The use of these massage articles, however, is often a strain for the user and is therefore limited to a relatively short time span. Body areas which are difficult to reach, for example certain parts of the back, can only be treated with the help of another person.

Moreover, DE 42 19 698 A1 discloses a therapeutic bandage for exerting pressure on a body part, with at least one pressure contact surface which can be applied to the relevant body part, and with at least one holding device for fixing the pressure contact surface under a static pressure. The pressure contact surface has individual spheres as massage projections which are embedded in a silicone composition in order to transmit forces. The massage projections can be acted upon by muscle force in order to generate reaction forces acting substantially directly on the body part concerned. The portions of the massage projections protruding from the silicone composition have the shape of rounded knobs.

In addition, U.S. Pat. No. 7,769,803 discloses a therapeutic bandage which is to be removably fixed by means of a closure element on a body part to be treated. To stimulate the body part, the therapeutic bandage is provided with rounded massage projections which come to rest on the body part to be treated.

Moreover, U.S. Pat. No. 5,381,558 and WO 97/49306 disclose an item of clothing which has massage projections which come to rest on a body part to be massaged.

In addition, FR-A-1 367 724 discloses a massage bandage with a hollow space for a therapeutic agent. DE 82 289 C discloses a therapeutic bandage which can be acted upon with stimulating current in the area of massage projections. Furthermore, U.S. Pat. No. 5,607,749 discloses a therapeutic bandage designed as a flat bandage with massage projections.

Finally, health plasters are known which are applied to the body part to be treated and release a therapeutic agent. The therapeutic agent is used up after a certain period, and the health plaster needs to be replaced with a new one, when necessary. As a result of the skin not tolerating an adhesive arranged on the health plaster, its use often leads to an allergic reaction of the body part to be treated.

It is an object of the invention to make available a therapeutic bandage which is of the type indicated at the outset and which permits targeted and prolonged massage therapy of a body part.

According to the invention, the object is achieved by the fact that the massage projections are designed as brushes.

The massage projections designed as brushes exert their therapeutic action throughout the period of time in which the therapeutic bandage is secured on the body part to be treated. The massage takes place without tiring the person wearing the therapeutic bandage and also without the help of other persons, in other words only by the movements which the wearer makes while wearing the therapeutic bandage, the use of brushes ensuring a relatively large surface area of contact with the body part to be treated. The action of the brushes can be adjusted by specific choice of the hardness of the bristles. If the therapeutic bandage has been applied correctly, only the moved body parts are massaged, for which reason irritation caused by the massage projections can be almost completely excluded. To support the action of the brushes, a therapeutic agent can also be applied manually either directly on the skin or onto the brushes, and this therapeutic agent is massaged into the skin as the therapeutic agent is being worn.

Alternatively, in the case of a therapeutic bandage with at least one therapeutic surface for a body part to be treated, on which there are massage projections pointing in the direction of the body part to be treated, and the therapeutic bandage is fixed removably on the body part by means of a closure element, and in which the massage projections are designed as rounded knobs, the object is achieved, according to the invention, by the fact that an acupuncture tip is arranged on the summit of the knob.

The acupuncture tip ensures an intensive stimulation of certain areas of the body part to be treated.

Each knob is preferably designed to be stiff, at least in the area of its summit. Because of the stiff design of the summit of the knob, it is possible to achieve a strong punctiform massage with a deep penetrating action.

In order to prevent painful pressing or sliding of the summit of the knob on the skin, an elastic transition area is expediently provided between the summit of the knob and the therapeutic surface. The elastic transition area ensures an at all times pleasant contact pressure of the summit of the knob on the body part to be treated.

An outer wall is preferably assigned to the therapeutic surface for the purpose of forming a hollow space which is provided with an inlet/outlet for a therapeutic agent. The therapeutic agent conveyed through the hollow space, for example warm water, intensifies the action of the therapeutic bandage. In addition to the stimulation by the massage projections, the body part to be treated is also relaxed by the warmth radiating through the therapeutic surface.

To allow a therapeutic agent in the form of an ointment, massage oil or the like to pass from the hollow space onto the skin of the body part to be treated, each knob or each brush is preferably assigned an outflow opening for the therapeutic agent connected to the hollow space. The therapeutic agent present in the hollow space is thus continuously removed from the knob or brush and massaged into the skin.

Each knob or brush is expediently mounted in the wall of the therapeutic surface. Each knob or brush is advantageously provided with a holder which comprises a sphere segment formed integrally on the underside of the knob or brush, a holder attachment directed coaxially away from the sphere segment and bearing a sealing cone, and a pressure cone connected to the sealing cone, where, in an unstressed state of the knob or brush, and as a result of a spring mat acting on the pressure cone, the sealing cone bears on a sealing seat of the therapeutic surface pointing in the direction of the outer wall, the holder attachment is received with play in a connecting bore, and the sphere segment lies in the therapeutic surface, spaced apart from a knob seat. In this way, in the unstressed state of the knob or brush, it is possible to ensure sealing of the therapeutic surface relative to the hollow space using a small number of component parts. At the same time, in the stressed state of the knob or brush, a passage is freed for the therapeutic agent to pass from the hollow space through the connecting bore to the therapeutic surface, and the contact pressure of the knob or brush is determined principally by the spring mat.

According to an advantageous development of the inventive concept, the knobs are part of an elastic sheet of knobs secured on the therapeutic surface, each knob being assigned a channel opening into the hollow space. This permits inexpensive production of the therapeutic bandage since the sheet of knobs together with the knobs is a single part which is produced in one production process and is secured on the therapeutic bandage. Through the channel opening into the hollow space, the stiffness of the knobs is determined as a function of the controllable pressure prevailing in the hollow space.

A valve is expediently fitted in the channel. The valve prevents an independent change of pressure within the associated knob. The valve is advantageously spring-loaded or designed with a locking device. The spring-loaded valve permits pressure-dependent filling of the associated knob. By contrast, permanent opening of the valve is ensured by means of the locking device.

According to a further advantageous embodiment of the invention, electrodes are provided in the area of the knobs and can be fed with stimulating current via supply lines. This provides for a combination of different therapeutic measures by which rapid healing is often achieved. For example, a therapeutic agent can be massaged into the skin by means of the knobs and at the same time treatment with stimulating current can be effected.

By being expediently designed as a flat bandage, it is possible for the therapeutic bandage to cover a relatively large body part to be treated, for example the chest or back. According to a further development of the invention, a therapeutic bandage which is particularly comfortable for the wearer and covers a large surface area is made available by designing it as a waistcoat, trousers or sleeve.

As the aim is to allow the therapeutic bandage to be fitted with minimum effort, the closure element is advantageously designed as a buttonhole strip cooperating with at least one button, or as a Velcro® closure.

It will be appreciated that the aforementioned features and those still to be discussed below can be used not only in the respectively indicated combination, but also in other combinations, without thereby departing from the scope of the present invention.

BRIEF DESCRIPTION OF THE DRAWINGS

FIG. 6 shows a view of a cross section along the line VI—VI according to FIG. 2, FIG. 7 shows a view of a cross section along the line VI—VI according to FIG. 2 in an alternative embodiment, FIG. 8 shows an enlarged view of a detail VIII according to FIG. 6 in an alternative embodiment, FIG. 9 shows an enlarged view of a detail IX according to FIG. 7 in a first alternative embodiment, FIG. 10 shows an enlarged view of a detail IX according to FIG. 7 in a second alternative embodiment, FIG. 12 shows an enlarged view of a detail XII according to FIG. 11.

DETAILED DESCRIPTION OF THE PREFERRED EMBODIMENTS

Figure 1:
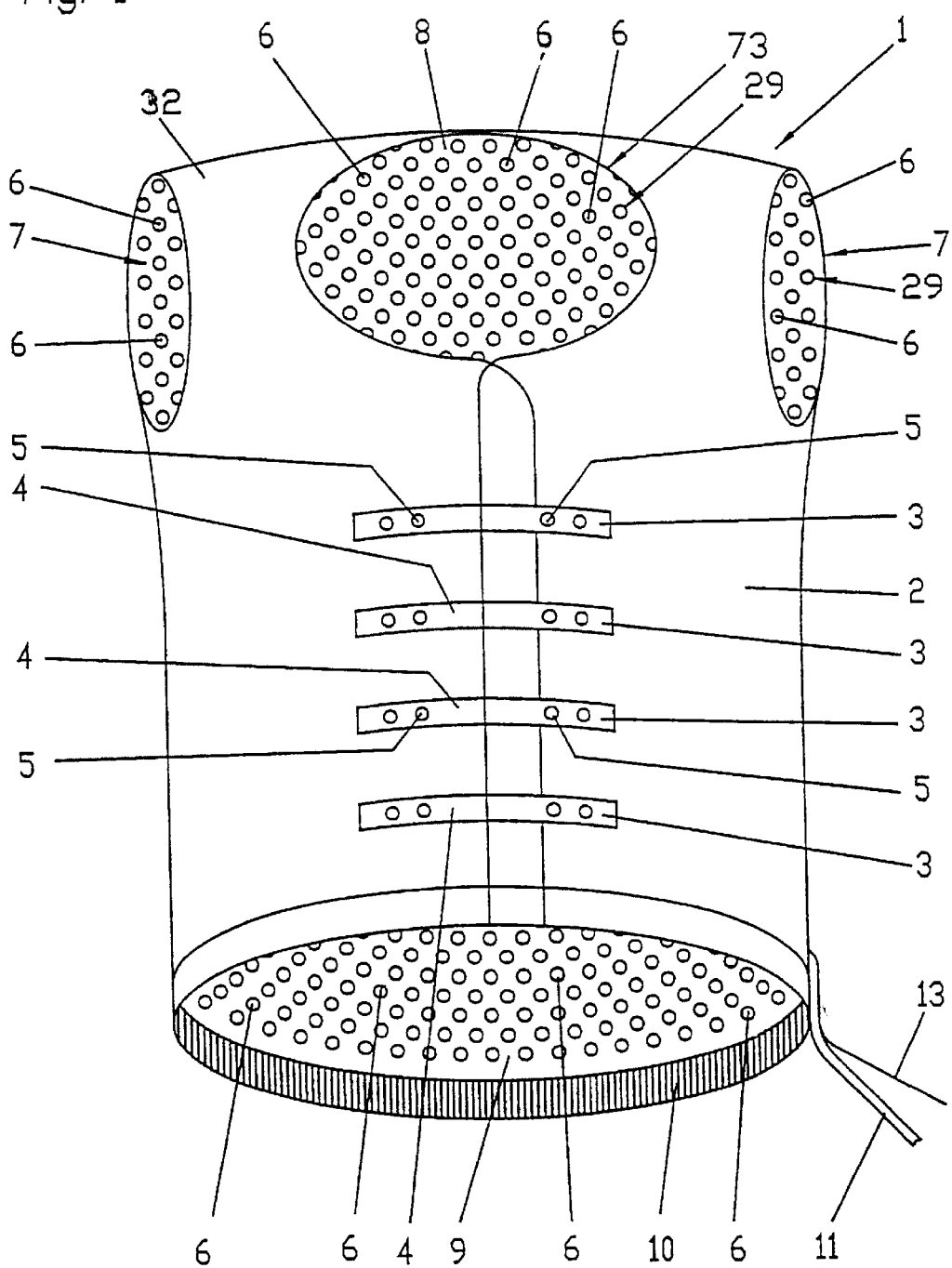
FIG. 1 shows a view of a therapeutic bandage according to the invention in a first embodiment.

FIG. 1 shows a therapeutic bandage 1 which is designed as a waistcoat 2, is adapted to the body shape of the wearer, and is held together via four closure elements 3 in the front area. The closure elements 3 are each designed as a buttonhole strip 4 cooperating with a button 5 fitted on the waistcoat 2, which is how the waistcoat 2 can be adapted to different body sizes. The waistcoat 2 is moreover provided with two armholes 7 and, when closed, has a neck opening 8 and a waist opening 9, said waist opening 9 being formed by a waistband 10 from which there emerge an inlet/outlet 11 for a therapeutic agent and a supply line 13 for supplying a stimulating current. The entire inner area of the waistcoat 2 forms a therapeutic surface 73 on which massage projections 29 designed as knobs 6 point in the direction of the body part 76 to be treated.

Figure 2:
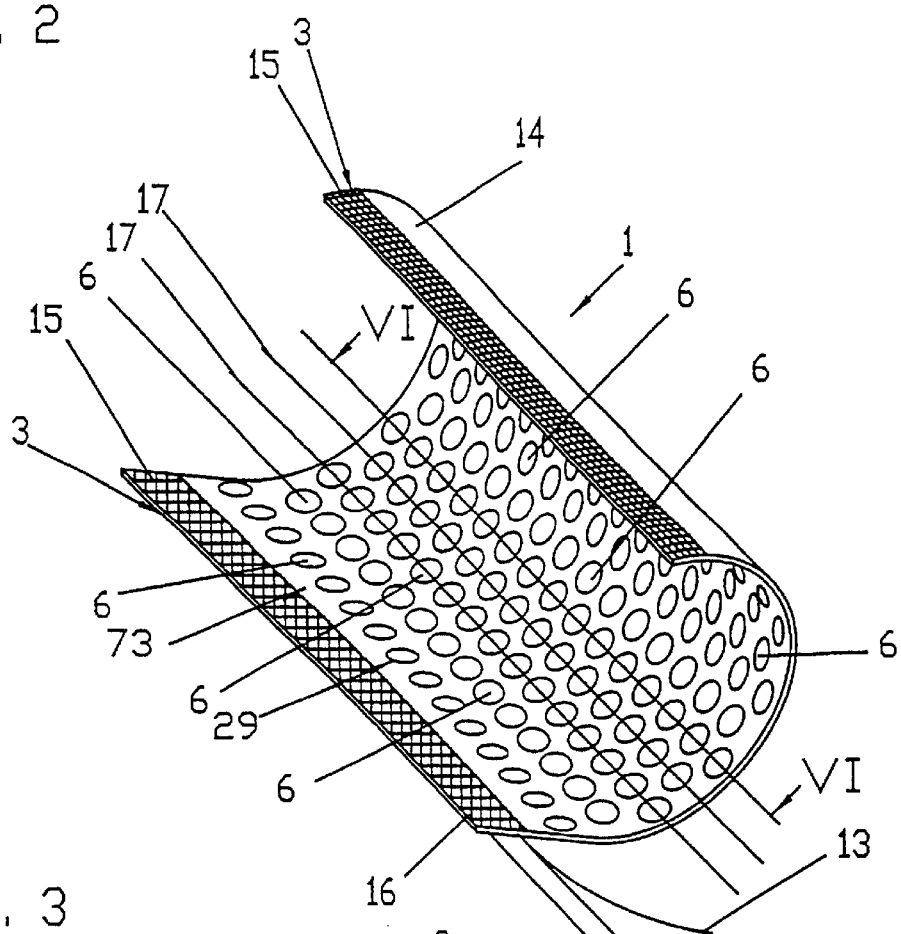
FIG. 2 shows a view according to FIG. 1 in a first alternative embodiment.

The therapeutic bandage 1 shown in FIG. 2 is a sleeve 14 which is fixed on the body part 76 to be treated by way of a closure element 3 designed as a Velcro® closure 15. The inlet/outlet 11, surrounded by a common sheath, and the supply lines 13 are incorporated in the area of a Velcro® tape 16 of the Velcro® closure 15. On the inwardly directed therapeutic surface 73 of the sleeve 14, rounded knobs 6 are once again arranged in staggered rows 17.

Figure 3:
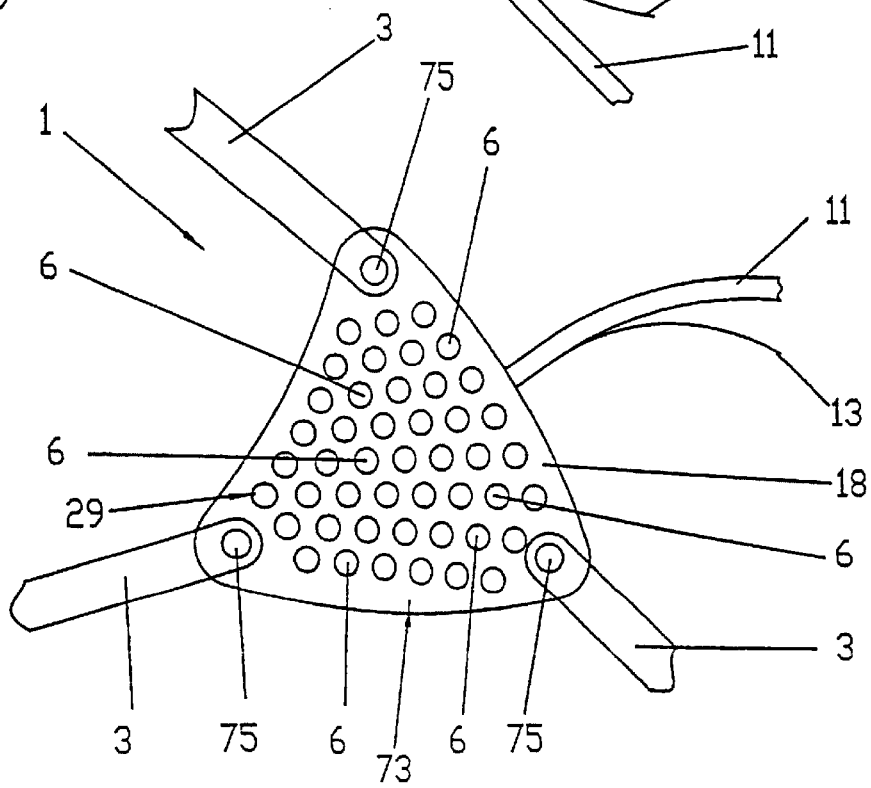
FIG. 3 shows a view according to FIG. 1 in a second alternative embodiment.

FIG. 3 shows a therapeutic bandage 1 which is designed as a flat bandage 18 and has a triangular shape, with closure elements 3 arranged via articulations 75 at its corners, by means of which closure elements 3 the flat bandage 18 is fixed on the body. By means of the articulations 75, the closure elements 3 can be pivoted in a direction adapted to the body. Rounded knobs 6 are arranged on the inwardly directed therapeutic surface 73 pointing in the direction of the body part 76 to be treated. The inlet/outlet 11 for the therapeutic agent and the supply lines 13 for the stimulating current are assigned to a reverse outer wall 32 of the therapeutic bandage 1.

Figure 4:
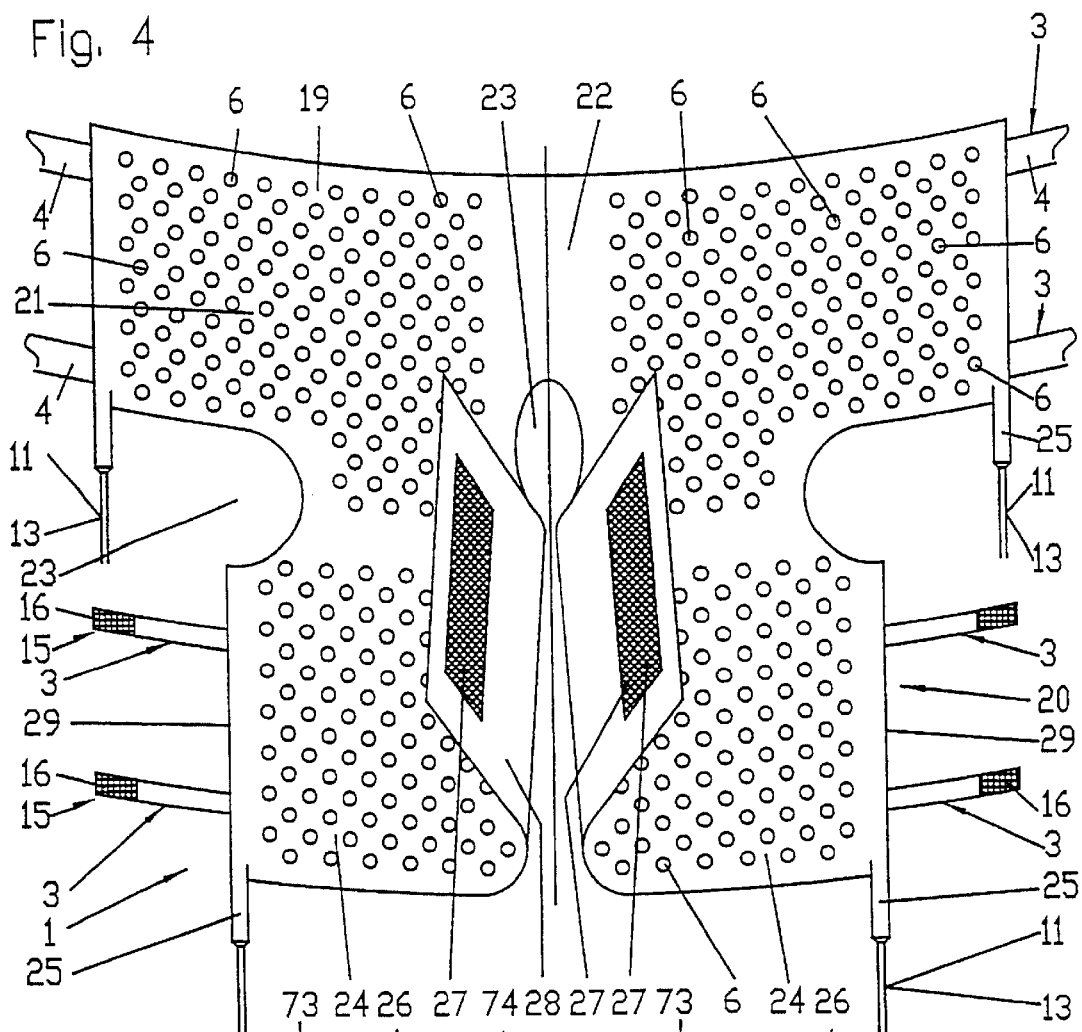
FIG. 4 shows a view according to FIG. 1 in a third alternative embodiment.

The therapeutic bandage 1 according to FIG. 4, when closed, is in the form of trousers 19. The trousers 19 are fixed by means of the closure elements 3, said closure elements 3 being Velcro® closures 15 on the trouser leg 20 and buttonhole strips 4 in the lower back area 21. To form the Velcro® closures 15, external Velcro® tapes 16 are provided on each trouser leg 20 and cooperate with a fleece tape 27 arranged on a support band 28. Each trouser leg 20 is designed as a leg sleeve 24 which joins directly to the lower back area 21 and carries the knobs 6 on the therapeutic surface 73. The therapeutic surface 73 of the lower back area 21 is likewise provided with rounded knobs 6, leaving a vertebral column area 22 free. Incorporated between the lower back area 21 and the trouser legs 20 there are cuttings 23 which make it possible to adapt the trousers 19 to different body shapes. The lower back area 21 has, like the trouser legs 20, in each case two inlets/outlets 11 and supply lines 13 for supplying stimulating current. The inlet/outlet 11 and the supply line 13 are joined to form a common connection 25 and communicate with a supply device (not shown) for the therapeutic agent and the stimulating current.

Figure 5:
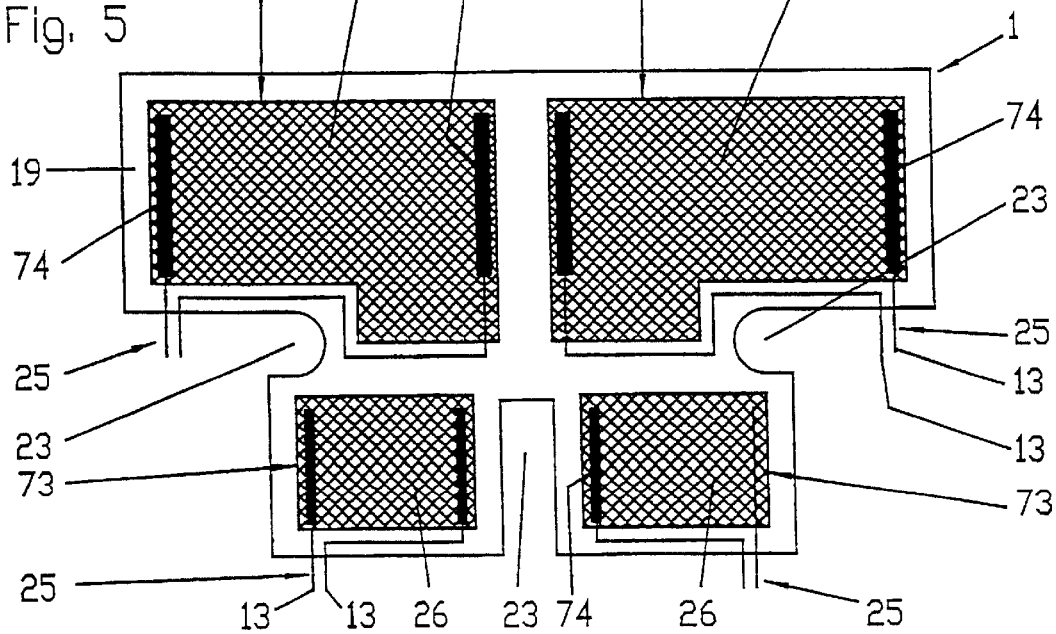
FIG. 5 shows a schematic view of the embodiment according to FIG. 4.

In the view of the trousers 19 according to FIG. 5, the therapeutic surface 73 provided with knobs 6 and indicated by cross-hatching is divided into several fields 26, each field 26 being provided with two spaced-apart electrodes 74 which communicate with supply lines 13 for the transfer of the stimulating current. The electrodes 74 can in this case be provided in a wall 30 of the therapeutic surface either alone or in addition to the knobs 6.

According to the cross section through the therapeutic bandage 1 illustrated in FIG. 6, the wall 30 of the therapeutic surface 73 carrying the knobs 6 is fixed to the outer wall 32 of the therapeutic bandage 1 by means of Velcro® connections 31. On the side directed toward the body part 76 to be treated, the knobs 6 have a stiffly configured summit 33. In a transition area 34 between the summit 33 of the knob 6 and the therapeutic surface 73, the knob 6 is elastic. When the therapeutic bandage 1 is in the applied state, the elastic transition area 34 provides a certain mobility of the summit 33 of the knob 6 initiated by the body movement of the person wearing the therapeutic bandage 1, giving a corresponding massage effect, and ensures that the summit 33 is restored to position when the therapeutic bandage 1 is not in the applied state.

In the therapeutic bandage 1 according to FIG. 7, the outer wall 32 is assigned to the therapeutic surface 73 in order to form a hollow space 35. Here, the wall 30 of the therapeutic surface 73 is sealed all round onto the outer wall 32 of the therapeutic bandage 1, and the outer wall 32 is provided with an inlet/outlet 11 for a therapeutic agent. By arranging a further inlet/outlet (not shown) in the outer wall 32, it is possible to convey the therapeutic agent in a circulation through the hollow space 35.

According to FIGS. 8 and 9, the massage projections 29 of the therapeutic bandage 1 are designed as brushes 36 and are secured on the wall 30 of the therapeutic surface 73. At the center of each of the brushes 36 there is an outflow opening 12 in the wall 30, through which a therapeutic agent introduced via the inlet/outlet 11 into the hollow space 35 is conveyed onto the skin of the body surface to be treated. The wetting of the skin is dependent on the diameter of the outflow opening 12 and on the pressure of the therapeutic agent in the hollow space 35.

The view according to FIG. 10 shows knobs 6 which are component parts of an elastic sheet 37 of knobs secured sealingly on the wall 30 of the therapeutic surface 73. Depending on the elasticity of the sheet 37 of knobs and on the pressure prevailing in the hollow space 35, knobs 6 of greater or lesser size and stiffness are formed, as is indicated by the broken lines. The elastic transition area 34 is present between the summit 33 of the knob 6, provided with a thickening 38, and the therapeutic surface 73.

At the center of each knob 6, a channel 39 opening into the hollow space 35 is incorporated in the wall 30 of the therapeutic surface 73, which channel 39 permits passage of the therapeutic agent out of the hollow space 35 and into the knob 6. A valve 40 is fitted in the channel 39 for the purpose of opening and closing it, said valve 40 comprising a valve tube 41 with a shoulder 42 at each end, said shoulders 42 receiving between them the wall 30, the hollow space 35 and the outer wall 32. Fitted in the valve tube 41 there is a valve plunger 43 which, in order to provide a seal relative to the valve tube 41, has two spaced-apart O-ring seals 45 arranged in corresponding grooves 44. The O-rings seals 45 slide along the tube wall 46 of the valve tube 41 and close/open a passage between the hollow space 35 and the valve tube 41 or between the hollow space 35 and the associated knob 6, which is produced via two bores 47 incorporated in the valve tube 41.

In the closed state of the valve 40 in which the passage between the hollow space 35 and the associated knob 6 is blocked, the valve plunger 43 plunges completely into the channel 39 and a limit stop member 48 of the valve plunger 43 comes to bear on the associated shoulder 42 of the valve tube 41. The O-rings seals 45 arranged on the valve plunger 43 here enclose between them the bores 47 incorporated in the channel 39. A button 49 is formed integrally on the limit stop member 48 of the valve plunger 43, with interposition of a cut-in 50. Arranged on the outer wall 32 of the therapeutic bandage 1 there is an elastic mat 51 which is provided with a number of holes 52 corresponding to the number of valves 40, and a cut-in 50 of an associated valve 40 lies in each hole 52. On account of the prestressing of the elastic mat 51, the valves 40 are at all times situated in the closed state, for which reason there is a constant pressure inside the knob 6.

To change the pressure prevailing in the knob 6, the valve plunger 43 is withdrawn from the valve tube 41 until the O-ring seal 45 directed toward the knob 6 frees the bores 47 and the therapeutic agent can pass from the hollow space 35 into the knob 6. The valve 40 is opened by means of gripping the button 49 counter to the restoring force exerted by the mat 51 on the limit stop member 48. After the button 49 is released, the valve 40 is automatically restored to the closed state. The valve 40 can also be assigned a locking device (not shown) which holds the valve 40 in the opened position. Thus, a change of pressure inside the hollow space 35 acts directly on the associated knob 6.

Figure 11:
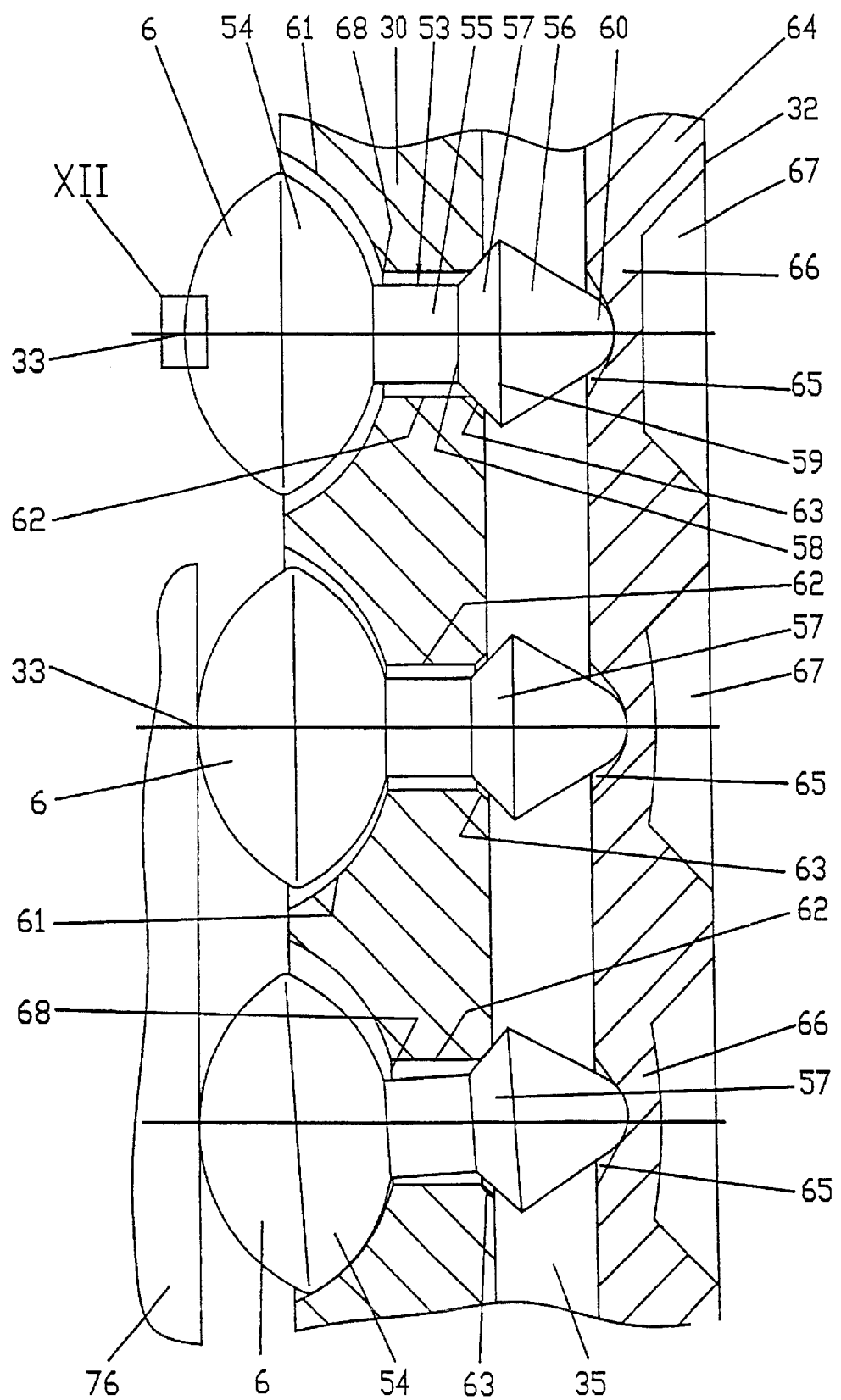
FIG. 11 shows an enlarged view of a detail IX according to FIG. 7 in a third alternative embodiment.

The knobs 6 shown in FIG. 11 are of solid design and are mounted in the wall 30 of the therapeutic surface 73 by means of a holder 53. The holder 53 includes a sphere segment 54 formed integrally on the underside of the knob 6, a holder attachment 55 coaxially adjoining the sphere segment 54 and bearing a sealing cone 57, and a pressure cone 56 which adjoins the sealing cone 57. The sealing cone 57 is integrally formed on the holder attachment 55 via its smallest diameter 58, which corresponds to that of the holder attachment 55, and its diameter increases in the direction away from the knob 6. At the greatest diameter 59 of the sealing cone 57, the pressure cone 56 joins it with the same diameter, which pressure cone 56 has the shape of a frustum of a cone with a rounded tip 60. A knob seat 61 is set into the wall 30 of the therapeutic surface 73, in which knob seat 61 the sphere segment 54 lies with play. Coaxially adjoining the knob seat 61 there is a connecting bore 62 which receives the holder attachment 55 with play. In the direction away from the knob seat 61, the wall 30 has a sealing seat 63 with an inclination which corresponds to the inclination of the sealing cone 57 of the knob holder 53. On that side of the wall 30 directed away from the therapeutic surface 73 is the hollow space 35 which is delimited by a spring mat 64 arranged parallel to the wall 30. The spring mat 64 profiled in cross section corresponds to the outer wall 32 of the therapeutic bandage 1 and acts on the knob holder 53. In the area of each pressure cone 56, the spring mat 64 has an indentation 65, the wall 66 of the spring mat 64 in the area of the indentation 65 being additionally narrowed by a depression 67 lying opposite the indentation 65, in order to permit an easy inward springing movement of the knob 6 upon loading. To fit the knob 6, the sealing cone 57 of the holder attachment 55 is forced through the elastically widening connecting bore 62. After the large diameter 59 of the sealing cone 57 has passed through, the connecting bore 62 is restored to position, after which the knob 6 is held safely in the wall 30.

By means of the action of the spring mat 64, the pressure cone 56 is forced into the sealing cone 57, and the connecting bore 62 is closed relative to the hollow space 35. If the knob 6 is now subjected to loading in the axial direction by a body part 76 to be treated, the knob 6 is forced partially into the knob seat 61 counter to the action of the spring mat 64. In this way, the sealing cone 57 moves away from the pressure cone 56, and the connecting bore 62 is opened, for which reason a therapeutic agent can flow out of the hollow space 35 and wet the skin of the body part 76 to be treated. As the load on the knob 6 increases, the sphere segment 54 comes to bear on the surrounding edge 68 of the connecting bore 62 and seals relative to the connecting bore 62. If, in this position of the knob 6, therapeutic agent is to escape from the hollow space 35, the sphere segment 54 must be provided with axially extending furrows. If the knob 6 is subjected to a non-axially oriented load by the body part 76 to be treated, it tilts in the bearing between the pressure cone 56 and the sealing cone 57 until the sphere segment 54 comes to bear partially in the knob seat 61. In this process, the connecting bore 62 is partially freed and the therapeutic agent can flow out of the hollow space 35. If there is no load acting on the knobs 6, the holder attachments 55 are restored to their position as a result of the spring action of the mat 51 and the connecting bores 62 are closed.

FIG. 12 shows a considerable enlargement of the summit 33 of the knob 6, from the center of which an acupuncture tip 69 issues. The acupuncture tip 69 comprises a ball 72 which is integrally formed on a shaft 70, said shaft 70 being connected to the summit 33 via a radius 71.

| List of reference numbers | |
|---|---|
| 1 | Therapeutic bandage |
| 2 | Waistcoat |
| 3 | Closure element |
| 4 | Buttonhole strip |
| 5 | Button |
| 6 | Knob |
| 7 | Armhole |
| 8 | Neck opening |
| 9 | Waist opening |
| 10 | Waistband |
| 11 | Inlet/outlet |
| 12 | Outflow opening |
| 13 | Supply line |
| 14 | Sleeve |
| 15 | Velcro closure |
| 16 | Velcro tape |

| -continued | |
|---|---|
| List of reference numbers | |
| 17 | Row |
| 18 | Flat bandage |
| 19 | Trousers |
| 20 | Trouser leg |
| 21 | Lower back area |
| 22 | Vertebral column area |
| 23 | Cutting |
| 24 | Leg sleeve |
| 25 | Connection |
| 26 | Field |
| 27 | Fleece tape |
| 28 | Support band |
| 29 | Massage projection |
| 30 | Wall |
| 31 | Velcro connection |
| 32 | Outer wall |
| 33 | Summit |
| 34 | Transition area |
| 35 | Hollow space |
| 36 | Brush |
| 37 | Sheet of knobs |
| 38 | Thickening |
| 39 | Channel |
| 40 | Valve |
| 41 | Valve tube |
| 42 | Shoulder |
| 43 | Valve plunger |
| 44 | Groove |
| 45 | O-ring seal |
| 46 | Tube wall |
| 47 | Bore |
| 48 | Limit stop |
| 49 | Button |
| 50 | Cut-in |
| 51 | Mat |
| 52 | Hole |
| 53 | Knob holder |
| 54 | Sphere segment |
| 55 | Holder attachment |
| 56 | Pressure cone |
| 57 | Sealing cone |
| 58 | Diameter |
| 59 | Diameter |
| 60 | Tip |
| 61 | Knob seat |
| 62 | Connecting bore |
| 63 | Sealing seat |
| 64 | Spring mat |
| 65 | Indentation |
| 66 | Wall |
| 67 | Depression |
| 68 | Edge |
| 69 | Acupuncture tip |
| 70 | Shaft |
| 71 | Radius |
| 72 | Ball |
| 73 | Therapeutic surface |
| 74 | Electrode |
| 75 | Articulation |
| 76 | Body part |

What is claimed is:

1. A therapeutic bandage, comprising:

a bandage medium including at least one therapeutic surface for contacting a body part to be treated, said bandage medium being removably secured to said body part by means of a closure element, wherein said therapeutic surface includes massage projections which point in the direction of the body part to be treated, wherein each projection is mounted through he bandage medium, wherein each projection is provided with a holder which comprises a sphere segment formed integrally on an underside of the projection, a holder attachment directed coaxially from the sphere segment and bearing a sealing cone, and a pressure cone adjoining the sealing cone, where, in an unstressed state of the projection, and as a result of an adjacent spring mat acting on the pressure cone, the sealing cone bears on a sealing seat of the therapeutic surface, and wherein the holder attachment is received with play in a connecting bore, and wherein the spherical element lies along the therapeutic surface, spaced apart from a projection seat.

2. The therapeutic bandage as claimed in claim 1, wherein the massage projections are designed as rounded knobs.

3. The therapeutic bandage as claimed in claim 2, wherein each knob includes a summit portion and each knob is stiff in the area of its summit.

4. The therapeutic bandage as claimed in claim 2, further including an elastic transition area between the summit of the knob and the therapeutic surface.

5. The therapeutic bandage as claimed in claim 3, further including an acupuncture tip arranged on the summit of the knob.

6. The therapeutic bandage as claimed in claim 1, wherein the massage projections are designed as brushes.

7. The therapeutic bandage as claimed in claim 1, further including an outer member coupled to said bandage medium along an edge portion of the bandage medium, wherein a hollow space is created between said bandage medium and said outer member, said hollow space providing a residence for a therapeutic agent and wherein said hollow space is accessible by way of a tube.

8. The therapeutic bandage as claimed in claim 1, wherein each projection is assigned an outflow passage connected to a hollow space within said bandage medium, said outflow passage effective for conducting the flow of the therapeutic agent.

9. The therapeutic bandage as claimed in claim 1, wherein the projections are part of an elastic sheet of projections secured on the therapeutic surface, each projection being assigned a channel opening into a hollow space within said bandage medium.

10. The therapeutic bandage as claimed in claim 9, further including a valve fitted in the channel of each projection.

11. The therapeutic bandage as claimed in claim 10, wherein the valve is spring-loaded or designed with a locking device.

12. The therapeutic bandage as claimed in claim 1, further including electrodes provided in the area of the projections wherein said electrodes can be fed with stimulating electrical current via supply lines.

13. The therapeutic bandage as claimed in claim 1, wherein said bandage medium is generally flat.

14. The therapeutic bandage as claimed in claim 1, wherein said bandage medium is designed as a waistcoat, trousers or sleeve.

15. The therapeutic bandage as claimed in claim 1, wherein said closure element is designed as a buttonhole strip cooperating with at least one button or as a Velcro® closure.

* * * * *

UNITED STATES PATENT AND TRADEMARK OFFICE
CERTIFICATE OF CORRECTION

PATENT NO. : 6,700,031 B1
DATED : March 2, 2004
INVENTOR(S) : Matthias Hahn

It is certified that error appears in the above-identified patent and that said Letters Patent is hereby corrected as shown below:

Column 8,
Line 63, change "through he" to -- through the --.

Signed and Sealed this

Twenty-ninth Day of June, 2004

JON W. DUDAS
*Acting Director of the United States Patent and Trademark Office*